| United States Patent [19] | [11] Patent Number: 4,692,408 |
|---|---|
| Banks et al. | [45] Date of Patent: Sep. 8, 1987 |

[54] FERMENTATION PROCESS FOR THE PRODUCTION OF POLYSACCHARIDES

[75] Inventors: Geoffrey T. Banks, Horsham; Paul D. Browning, Orpington, both of United Kingdom

[73] Assignee: Imperial Biotechnology Limited, London, England

[21] Appl. No.: 556,020

[22] Filed: Nov. 29, 1983

[30] Foreign Application Priority Data

Nov. 30, 1982 [GB] United Kingdom ................. 8234111

[51] Int. Cl.$^4$ ...................... C12P 19/08; C12P 19/04; C12Q 3/00; C12N 1/38; C12R 1/64
[52] U.S. Cl. .................................... 435/104; 435/101; 435/3; 435/813; 435/819; 435/910; 435/244
[58] Field of Search .................. 435/3, 101, 104, 813, 435/910, 819, 102, 244; 252/8.55 D; 166/246

[56] References Cited

U.S. PATENT DOCUMENTS

| | | | |
|---|---|---|---|
| 3,251,749 | 5/1966 | Lipps, Jr. ............................ | 435/104 |
| 4,355,106 | 10/1982 | Lawford ............................ | 435/101 |
| 4,400,466 | 8/1983 | Azoulay ............................. | 435/101 |
| 4,400,467 | 8/1983 | Bauer et al. ........................ | 435/104 |

OTHER PUBLICATIONS

G. W. Pace and R. C. Righelato, "Advances in Biochemical Engineering" vol. 15, 1980, pp. 29–68.

*Primary Examiner*—Esther M. Kepplinger
*Attorney, Agent, or Firm*—Scully, Scott, Murphy & Presser

[57] ABSTRACT

Polysaccharides, such as xanthan gum, are produced by culturing microorganisms, e.g. of the Xanthomonas genus, in a two stage process. In the first stage, growth of the microorganism is favored, e.g. by using a predetermined quantity of a carbon-containing nutrient which does not support biosynthesis of the polysaccharide. In the second stage, the conditions are such that biosynthesis of the polysaccharide takes place with substantially no growth of the microorganism, e.g. by adding carbohydrate in the absence of nutrient required for polysaccharide growth.

By this process, the requirement for oxygen is greatly reduced at the time when the culture medium has its highest viscosity, thereby minimizing problems of low oxygen transfer capability in viscous media.

8 Claims, No Drawings

FERMENTATION PROCESS FOR THE PRODUCTION OF POLYSACCHARIDES

FIELD OF THE INVENTION

This application describes a new process for the production of polysaccharides, especially xanthan gum, by fermentation. Xanthan gum is a polyanionic polysaccharide used as a thickener and emulsifier in the food, pharmaceutical and cosmetic industries. It is also used by the oil industry as a component of drilling mud and as an agent for tertiary oil recovery. The present world market for xanthan gums is about 10,000 tonnes per annum valued at about 70,000,000.

BACKGROUND OF THE INVENTION

Xanthan gum is produced commercially by batch fermentation in submerged culture. *Xanthomonas juglandis* and *X. campestris* are examples of suitable organisms. Culture fluids develop extremely high viscosity and pseudoplasticity, which have a seriously detrimental affect on the oxygen transfer capabilities of conventionally designed and operated fermenters. This inevitably leads to the fermentation becoming limited by the oxygen transfer rate supported by the reactor and results in low xanthan yields and extended fermentation times.

The above difficulties could, in theory, be overcome in two different ways:

(i) by improvements in fermenter design, resulting in higher aeration efficiencies.

(ii) by controlling the oxygen demand of the culture without affecting productivity.

This invention is concerned with the latter approach. Polysaccharide biosynthesis is an energy-consuming process and oxygen is therefore required during fermentation for both growth and xanthan biosynthesis, which occur simultaneously in the conventional batch processes. The oxygen requirements for the two processes may be estimated as follows:

(i) Oxygen required for cellular biosynthesis

When a typical prokaryotic microorganism grows aerobically on a medium in which glucose is the sole carbon source, approximately 50% of the carbon is catabolised to produce carbon dioxide and water with the generation of ATP.

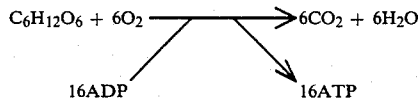

The remaining carbon is metabolised to produce cellular material. Thus for every mole of glucose utilised for cellular biosynthesis, 3 moles of diatomic oxygen are required. The figure of 16 moles of ATP per mole of glucose is a generally accepted figure for prokaryotic microorganisms.

(ii) Oxgen required for xanthan biosynthesis

The biosynthetic pathway of xanthan gum is not fully understood but it is generally considered that the addition of a single hexose monomer unit to the xanthan polymer requires two molecules of ATP.

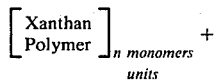

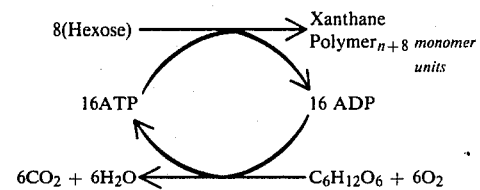

Thus, for every 9 moles of glucose utilised for xanthan biosynthesis, 6 moles of diatomic oxygen are required.

From these estimates it can be deduced that cellular biosynthesis requires 4.5 times more oxygen than xanthan biosynthesis.

The objective of the present invention is to regulate the oxygen demand by the separation of growth and product biosynthesis using a two-stage fermentation process. In the first stage, conditions are employed that permit growth of the organism but not xanthan biosynthesis. Since a high viscosity will not develop in the absence of polysaccharide, the relatively high oxygen demand, similar to that experienced to conventional fermentations, can be met without problems. In the second stage, growth will be prevented and only polysaccharide biosynthesis will occur. Although a high viscosity will inevitably develop, the oxygen demand of the culture will be significantly lower than in conventional processes since energy will not be required for growth but only xanthan biosynthesis. The oxygen requirement of the organism will thus be more easily satisfied. Furthermore, by controlling the amount of growth occurring in the first stage, the oxygen demand during the second stage may actually be regulated.

DISCUSSION OF THE PRIOR ART

No. GB-1513061 discloses a process for the continuous production of polysaccharides of the alginic acid type in which a bacterium of the species *Azotobacter vinelandii* is cultivated under conditions such that the concentration of saccharide carbon source is limiting on growth of the bacterium, polysaccharide biosynthesis being simultaneous with bacterial growth. In this process, oxygen supply is related to the efficiency with which the monosaccharide or disaccharide carbon source is converted into the polysaccharide product, limitation of the oxygen supply limiting growth of the bacteria.

U.S. Pat. No. 3,328,262 describes a continuous process for polysaccharide synthesis in which cells of an appropriate organism are initially grown in a low carbohydrate medium, with little formation of the polysaccharide. The cells were then fed to a reactor for the formation of polysaccharide, in a continuous procedure, fresh culture medium being fed into the reactor as the polysaccharide-containing product was run off. In such a process, continued growth of the micoorganism will proceed with the synthesis of the polysaccharide. In this way a continuous culture was possible without the organisms losing their ability to synthesize the polysaccharide.

SUMMARY OF THE INVENTION

The present invention provides a method for the synthesis of polysaccharides by culturing polysaccharide-producing microorganisms in a nutrient-containing medium which comprises culturing said microorganisms in a first stage under conditions such that growth of the microorganisms takes place preferentially with restricted polysaccharide synthesis, and in a second stage, polysaccharide synthesis takes place with substantially no growth of the microorganisms.

DETAILED DESCRIPTION OF THE INVENTION

In one preferred embodiment, the first stage is conducted until growth of the microorganism substantially ceases in the presence of a predetermined quantity of carbon-containing nutrient, which do not support polysaccharide biosynthesis, e.g. glycerol or xylose.

In another embodiment, the first stage is accomplished in at least two consecutive fermentation vessels, in the first of which a continuous culture is employed, and in the second of which growth is restricted by the rate of supply of carbon-containing nutrients until such time as further growth of the culture becomes limited by an element other than carbon. The growth of the microorganisms in the continuous culture can also be limited by carbon containing nutrients.

In a preferred embodiment, a carbohydrate is added in the first stage continuously at a rate that increases exponentially as the multiplication of the microorganisms takes place.

In all embodiments, the second stage can be conducted by adding a carbohydrate to the medium, in a single portion or at intervals as synthesis of the polysaccharide takes place, in the exclusion of one or more nutrients required for growth of the microorganisms.

Preferably the microorganisms are of the genus Xanthomonas, more preferably of the species *Xanthomonas campestris* or *Xanthomonas juglandis*. Other Xanthomonas species that can be used include *Xanthomonas begoniae, Xanthomonas carotae, Xanthomonas hederae, Xanthomonas incanae, Xanthomonas malvacearum, Xanthomonas papavericola, Xanthomonas phaseoli, Xanthomonas pisi, Xanthomonas translucens, Xanthomonas vasculorum* and *Xanthomonas vesicatoria*.

Whilst the invention is especially applicable to production of xanthan gum using organisms of the Xanthomonas genus, it is also applicable to the production of other microbial exopolysaccharides, e.g. the production of pullulan by organisms of the Aureobasidium genus, and the production of Alginic acid by organisms of the genus Azotobacter.

A number of methods of implementing the invention are possible. In each, the first objective is, of course, to permit rapid growth whilst preventing xanthan production. Having achieved this, the second objective is then to permit xanthan production whilst preventing growth. The first objective is the more difficult of the two to achieve.

One method of achieving growth without xanthan biosynthesis involves the use of carbon sources that do not support xanthan production, the composition of the medium being carefully balanced so that one element that is essential for growth (other than carbon, which is also essential for xanthan biosynthesis) becomes exhausted at the end of the first stage. This element is preferably nitrogen, although other minerals such as phosphorus, potassium, sulphur, magnesium or calcium may also be used.

In a second method, a carbon source that supports both growth and xanthan production is used. The method of cultivation is, however, designed to limit the specific growth rate below the maximum by restricting the supply of the carbon substrate. When the supply of carbon substrate is restricted, that material which is available will be diverted to cellular biosynthesis at the expense of xanthan production. As before, growth is maintained until a selected element, again preferably nitrogen, is exhausted, at which point further growth cannot occur.

The second stage is the same for both methods; excess nutrient, preferably glucose, is added and the culture is incubated with aeration and agitation whilst xanthan production occurs. This is illustrated below in Example 1. It is not essential to use glucose at this stage; any carbon source that will support gum production, for example, fructose, sucrose, lactose or starch, may also be used.

In the first method, care must be taken in the selection of the organism and carbon source so that the carbon source supports good growth of the organism but not xanthan biosynthesis. In selecting a combination of organism and carbon source for use in the first stage, both the cost of the carbon source and the productivity of the organism when grown on glucose were taken into consideration.

Combinations that may be employed include:

| Organism | Carbon Source |
| --- | --- |
| X. juglandis NCPPB 413 | Glycerol |
| X. juglandis NCPPB 1447 | Glycerol |
| X. juglandis NCPPB 1059 | Glycerol |
| X. juglandis ICPB XJ 107 | Glycerol |
| X. campestris NCIB 11781 | Glycerol |
| X. juglandis ICPB XJ 107 | Xylose |
| X. campestris NCIB 11781 | Xylose |

Another version of this process may involve supplementing the carbon source used in the first stage with a crude protein or protein hydrolysate. Providing this does not radically alter the overall elemental balance such that carbon becomes limiting at the end of the first stage, this may improve the process by increasing the specific growth rate and reducing the duration of the first stage.

Processes employing the second method rely on the specific growth rate being limited throughout the first stage by the supply of carbon-containing nutrients. The conventional method to achieve this is by continuous culture. Example 2 is a demonstration of the first stage of such a process; stage 2 was omitted. The second stage will require one or more additional fermenters in which the overflow from the continuous fermenter is collected and growth without xanthan biosynthesis continued (by any of the other methods described) until an element other than carbon becomes limiting. Finally the culture will be mixed with a carbon-containing nutrient, e.g. glucose or other carbohydrate e.g. lactose that will support xanthan biosynthesis, and incubated with aeration and agitation. Whilst the first stage must be operated continuously the second stage may be operated either continuously or semi-batchwise.

Alternatively, the entire process may be carried out batchwise by limiting the specific growth rate by means of a concentrated feed of the carbon containing nutrients. If the rate of feeding is increased exponentially, that is, governed by a relationship such as:

$$f = f_0 e^{kt}$$

where
t = time
f = feed rate at time t
$f_o$ = feed rate at t = o
k = exponential constant with units of reciprocal time
then whilst growth will be limited throughout the first stage by the feed, the specific growth rate will be maintained at a constant predetermined level numerically equal to or less than the constant k. The feed is maintained until growth is stopped by the exhaustion of an element not present in the feed, typically nitrogen. At this point the second stage is commenced simply by adding an excess of glucose or other suitable carbon source to the fermenter and incubating with aeration with agitation. A process of this particular type is compared directly with a conventional fermentation in Example 3.

Further versions of both continuous and fed-batch processes may be devised by supplementing the feed with a small amount of protein or protein hydrolysate as a source of growth factors enabling higher specific growth rates to be achieved. This will result in increased output of the continuous process or reduced fermentation times of the batch process. The latter type of process is demonstrated by Example 4.

Hybrid processes employing both methods are also possible.

Proteins and protein hydrolysates are known to support high specific growth rates without xanthan biosynthesis taking place. Unfortunately, the carbon to nitrogen ratio of this class of nutrients is such that carbon always becomes limiting first. It is possible, however, to devise processes which employ proteins or protein hydrolysates providing that a short intermediate stage is introduced; making the process a three stage one. During the first stage the organism grows at its maximum specific growth rate, utilising the proteinaceous material, until carbon becomes limiting. Then, during the short intermediate stage, the growth rate is limited by a nitrogen-deficient carbon containing nutrient supplied as a concentrated feed until nitrogen becomes exhausted. At this point growth can no longer take place and the final stage can be commenced by adding an excess of glucose or other suitable carbon source to the fermenter and incubating with aeration and agitation. The entire process takes place within a single fermentation vessel. It is an advantage of this invention that, except in the embodiment involving continuous culture, a single vessel can be used for the entire fermentation process.

The product may be separated from the culture by any convenient method known in the art or the whole culture may be used with or without previously killing the bacteria, depending on the intended use.

In the following Examples, the following media are used:

| | % (w/v) |
|---|---|
| Agar A | |
| Oxoid meat extract | 3.00 |
| Oxoid peptone L37 | 0.50 |
| Oxoid yeast extract | 0.50 |
| Oxoid Bacto agar | 2.00 |

| | % (w/v) |
|---|---|
| Distilled water to volume | |
| pH adjusted to 7.4 with sodium hydroxide | |
| sterilisation: 20' at 121° C. | |
| Dispense: 7 ml per bijou bottle and | |
| slope whilst allowing agar to set. | |
| Medium - B | |
| KH$_2$PO$_4$ | 0.65 |
| MgSO$_4$.7H$_2$O | 0.0375 |
| FeSO$_4$.7H$_2$O | 0.005 |
| ZnSO$_4$.7H$_2$O | 0.001 |
| MnSO$_4$.4H$_2$O | 0.001 |
| Oxoid Bacto Peptone | 0.64 |
| Distilled water to volume | |
| pH: 7.0 | |
| Medium - C | |
| KH$_2$PO$_4$ | 0.65 |
| MgSO$_4$.7H$_2$O | 0.0375 |
| FeSO$_4$.7H$_2$O | 0.005 |
| ZnSO$_4$.7H$_2$O | 0.001 |
| MnSO$_4$.4H$_2$O | 0.001 |
| Sigma Casein Hydrolysate (enzymatic) | 0.715 |
| Mains water to volume | |
| pH: 6.5 | |

Growth was estimated spectrophotometrically at 600 nm, and by measuring the dry weight of a 25 ml sample. Oxygen demand was calculated from the time taken for the dissolved oxygen content of a saturated sample to fall to zero.

Crude polysaccharide yields were measured by precipitatable material from culture broth by the addition of 0.1 volumes of 22% (w/v) potassium chloride and 2 volumes of isopropanol, filtering, washing with 67% aqueous isopropanol, and drying.

Oxygen uptake was determined by comparative analysis of the oxygen content of the entry and exit gas streams, to and from the fermenter.

The *Xanthomonas campestris* used in the following Examples is of the strain NC1B 11781 deposited at the National Collection of Industrial Bacteria, Aberdeen.

EXAMPLE 1

Cells of *X. juglandis* NCPPB413 prepared as a slant culture on Agar A were suspended in 9 ml of sterile 0.9% saline solution. Two 500 ml conical flasks each containing 100 ml of sterile medium B were each inoculated with 2 ml of the saline suspension. These seed cultures were incubated with aeration by shaking for 1 day at 30° C. Each seed culture was then used to inoculate a New Brunswick model F-05 fermenter, each fermenter being identically batched with 3.4 L of sterile medium containing glycerol, 20 g/L; potassium dihydrogen phosphate, 5 g/L; ammonium sulphate, 2 g/L; citric acid, 2 g/L; boric acid, 6 mg/L; magnesium sulphate (heptahydrate salt) 0.2 g/L; zinc sulphate (heptahydrate salt, 21.2 mg/L; ferric chloride (hexahydrate salt), 2.4 mg/L; calcium chloride (dihydrate salt), 43.8 mg/L; in distilled water. Sterile air was supplied at the rate of 2 L per minute and the culture stirred at 400 r.p.m. The temperature was maintained at 30° C. and the pH at 7.0. The sole source of nitrogen was ammonium sulphate and when this had been fully utilised, a sterile concentrated solution containing 102 g of glucose was added to each fermenter. This level was chosen entirely arbitrarily and there is no reason why a higher level could not be used in a commercial production process. The results are given in Table 1 in which the two fermenters are identified as fermenter A and fermenter B. The final yields of polysaccharide were 2.7–3.0%.

It will be seen that, once the first stage has been completed, as shown by the reduction of the ammoniacal nitrogen content to zero, and the glucose has been added, the formation of xanthan takes place, as shown by the disappearance of glucose, and the increase in the consistency coefficient.

EXAMPLE 2

Cells of *X. campestris*, (NC1B 11781) prepared as a slant culture on Agar A were suspended in 9 ml of sterile 0.9% saline solution and 2 ml of the suspension used to inoculate 100 ml of sterile medium B in a 500 ml conical flask. This seed culture was incubated with aeration by shaking for 1 day at 30° C. after which 45 ml was then used to inoculate a 1 liter fermenter containing 900 ml of sterile medium composed of glucose, 6.67 g/L; Oxoid casein hydrolysate (L41), 5 g/L; ammonium sulphate, 4.0 g/L; potassium dihydrogen phosphate, 5.0 g/L; magnesium sulphate (heptahydrate salt), 0.46 g/L; boric acid, 12 mg/L; zinc sulphate (heptahydrate salt), 21.2 mg/L; ferric chloride (hexahydrate salt), 58 mg/L; calcium chloride (dihydrate salt), 110 mg/L; and distilled water. The culture was allowed to grow batchwise for 21 hours at 30° C. and then flow of the feed medium was started to give a dilution rate of 0.07 per hour. The feed medium was of the same composition except that the level of casein hydrolysate was lower; 1 g/L. The culture was maintained at 30° C. and the pH controlled automatically at 7.0 throughout the fermentation which was terminated after six days. Under steady-state conditions the culture broth was non-viscous (the consistency coefficient was 0.065 g cm$^{-1}$ sec$^{n-2}$; the flow behaviour index was 0.83), the dry cell weight was 2.0 g/L and the glucose concentration less than 0.1 g/L.

EXAMPLE 3

Cells of *X. campestris* (NC1B 11781) prepared as an agar slant culture were suspended in 9 ml of sterile 0.9% saline solution and 2 ml of the suspension used to inoculate 100 ml of sterile medium B in a 500 ml conical flask. This seed culture was incubated with aeration by shaking for 1 day at 30° C. This seed was then used to inoculate 1 L of sterile medium B in a 4 L conical flask. This secondary seed culture was again incubated with aeration by shaking for 1 day at 30° C. This was then used to inoculate 400 L of sterile medium C in a fermenter of conventional design. This culture was grown at 30° C.; sterile air was supplied at the rate of 200 L per minute and the culture was stirred at 153 r.p.m. After 27 hours two further fermenters of identical design (fermenter C and fermenter D) each containing 360 L of sterile medium were each inoculated with 40 L of culture. The medium in fermenter C was composed of glucose, 43 g/L; ammonium sulphate, 1.5 g/L; potassium dihydrogen phosphate, 5 g/L; magnesium sulphate (heptahydrate salt), 0.46 g/L; boric acid, 12 mg/L; zinc sulphate (heptahydrate salt), 21 mg/L; ferric chloride (hexahydrate salt) 58 mg/L; calcium chloride (dihydrate salt), 110 mg/L; in mains water. The medium in fermenter D was identical except that the glucose was omitted at batching and the same amount added during the course of the fermentation by means of a feed and an addition of sterile glucose solution. Immediately after inoculation a feed to fermenter D of a sterile glucose solution containing 93.4 g/L was commenced at an initial flow rate of 1 ml per minute. The flow was increased exponentially under computer control with an exponential constant of 0.07 per hour. Once the flow rate reached 50 mls per minute it was held constant until a total volume of 50 L had been fed into fermenter D. At this point an addition of a concentrated sterile solution containing 10.8 Kg. of glucose was made to the fermenter. The operation of both fermenters was identical; sterile air was supplied at the rate of 200 L per minute and the cultures stirred at 153 r.p.m. The temperature was maintained at 30° C. and pH at 7.0 by means of automatic control. The results are given in Table 2.

In fermenter C, where a conventional process is taking place, the glucose concentration drops throughout the process, and the consistency coefficient rapidly increases, showing that xanthan production is taking place. The oxygen demand and transfer rate are also initially high.

In fermenter D, in which the process of the invention is carried out, the consistency coefficient is low until the content of ammoniacal nitrogen falls substantially to zero, and the glucose addition is made, showing that during the exponential addition of glucose, substantially only cell formation is taking place.

The total amount of polysaccharide produced was substantially the same in each case as indicated by the measured rheology and polysaccharide precipitates. Fair comparisons can only be made at times of equivalent glucose concentration, that is, when equal amounts of glucose have been utilised in both processes.

Most importantly, the oxygen demand of the culture in Fermenter D was substantially lower than the control (Fermenter C) throughout the process.

By comparing the oxygen demands with the oxygen transfer rates actually achieved, it can be seen that the amount by which the oxygen transfer rate fails to meet the demand is substantial in the case of Fermenter C, whereas in the case of Fermenter D, the two are substantially equal.

EXAMPLE 4

The inoculum development procedure described in Example 3 was used to provide 400 L of seed culture, 40 L of which was used to inoculate 360 L of sterile medium in fermenter D. The medium had the same composition is that used in Fermenter D in Example 3. Immediately after inoculation a feed of sterile solution containing 93.4 g of glucose per liter and 4.3 g of casein hydrolysate (Oxoid L41) per liter was commenced at an initial flow rate of 2 ml per minute. The flow was increased under computer control with an exponential constant of 0.14 per hour. Once the flow rate had reached 100 ml per minute the feed was stopped and an addition of a concentrated sterile solution containing 10.8 Kg of glucose was made to the fermenter. The operation of the fermenter was identical to that described in Example 3. The results are given in Table 3.

After 48 hours, the polysaccharide yield was 1.6–2.0%. It will be seen that there is little polysaccharide formation until the glucose is added, as shown by the small increase in the consistency coefficient. Once the ammoniacal nitrogen had fallen nearly to zero and growth had stopped, the glucose was added, and polysaccharide synthesis took place, as shown by the considerable increase in the consistency coefficient.

TABLE 1

| | FERMENTER A | | | | | | FERMENTER B | | | | |
|---|---|---|---|---|---|---|---|---|---|---|---|
| LOG HOURS | I | II | III | IV | V | LOG HOURS | I | II | III | IV | V |
| 0 | .05 | .30 | | | | 0 | .08 | .24 | | | |
| 6 | .18 | .32 | | | | 6 | .23 | .32 | | | |
| 12 | .35 | .25 | | | | 12 | .59 | .24 | | | |
| 18 | .75 | .15 | | | | 18½ | .65 | .21 | | | |
| 21 | 1.3 | .28 | | | | 21 | .85 | .35 | | | |
| 24 | 1.5 | .20 | | | | 24 | 1.1 | .23 | | | |
| 30 | 2.1 | .26 | | | | 30 | 1.3 | .22 | | | |
| 36 | 2.9 | .19 | | | | 36 | 1.7 | .23 | | | |
| 41¾ | 3.9 | .08 | | | | 41¾ | 2.1 | .15 | | | |
| 45¼ | 4.7 | .01 | | | | 45¼ | 2.3 | .21 | | | |
| 48 | 5.5 | 0 | | | | 48 | 2.6 | .18 | | | |
| 48¾ | GLUCOSE ADDITION | | | | | 54 | 3.4 | .14 | | | |
| 50¾ | 5.0 | 0 | | .37 | .65 | 60 | 4.9 | .06 | | | |
| 54 | 5.2 | 0 | .99 | | | 63 | 5.9 | .01 | | .51 | .64 |
| 60 | 5.3 | 0 | .66 | | | 63 | GLUCOSE ADDITION | | | | |
| 65¾ | 5.4 | 0 | .54 | | | 65¾ | 5.6 | 0 | 1.15 | | |
| 72 | 4.3 | | .71 | | | 72 | 4.5 | | .28 | | |
| 90 | 5.0 | | .02 | | | 90 | 4.9 | | .15 | | |
| 114 | 5.1 | | .03 | | | 114 | 5.1 | | .03 | | |
| 138 | 3.7 | | .01 | 51.2 | .24 | 138 | 3.5 | | .02 | 92.5 | .21 |

I = Optical Density 600 nm
II = Ammoniacal Nitrogen mg ml$^{-1}$
III = Glucose % w/v
IV = Consistency Coefficient gm cm$^{-1}$ sec$^{n-2}$
V = Flow Behaviour Index (n)

TABLE 2

| | FERMENTER C (For Comparison) | | | | | | | FERMENTER D | | | | | | | |
|---|---|---|---|---|---|---|---|---|---|---|---|---|---|---|---|
| LOG HOURS | I | II | III | IV | V | VI | VII | LOG HOURS | I | II | III | IV | V | VI | VII | VIII |
| 0 | .27 | 3.9 | | | | | .57 | 0 | .39 | <.01 | | | | | | .36 |
| 6½ | .50 | 3.8 | | | .016 | .98 | 1.0 | 6½ | .61 | .01 | | | | <.01 | 1 | .47 |
| 12½ | 1.1 | | | | | | | 12½ | .76 | .01 | | | | | | |
| 18¼ | 1.6 | 3.5 | | | .31 | .68 | .77 | 18¼ | .95 | .01 | | | | <.01 | 1 | .67 |
| 21½ | 2.3 | | 12 | 6.7 | | | | 21½ | 1.3 | | | | | | | |
| 24½ | 3.2 | 3.1 | | | | | | 24½ | 1.4 | .07 | .30 | 3.2 | <.5 | | | |
| 30½ | 3.4 | 2.7 | | | 4.3 | .49 | 1.2 | 30½ | 1.7 | .08 | .28 | | | .04 | .85 | .68 |
| 36½ | 5.1 | 2.3 | | | | | | 36½ | 2.6 | .05 | .27 | | | | | |
| 42¼ | 5.6 | 2.0 | | | 22 | .35 | 1.8 | 42¼ | 2.8 | .06 | .23 | | | .32 | .67 | .85 |
| 48½ | 6.7 | 1.5 | 29 | 12 | | | | 48½ | 3.1 | .06 | .18 | 13 | 9 | | | |
| 54½ | 5.6 | 1.2 | | | 39 | .31 | 1.9 | 54½ | 3.4 | .21 | .08 | | | 3.9 | .49 | 1.0 |
| 57½ | 5.8 | | | | | | | 57½ | 4.8 | | GLUCOSE ADDITION | | | | | |
| 60½ | 6.0 | 1.0 | | | | | | 60½ | 4.9 | 2.1 | 0 | | | | | |
| 66¼ | 5.4 | 1.0 | | | 58 | .28 | 2.1 | 66¼ | 5.2 | 1.7 | | | | 26 | .33 | 1.4 |
| 69½ | 5.5 | | 24 | 8.5 | | | | 69½ | 4.8 | | | | | | | |
| 72½ | 7.1 | .85 | | | | | | 72½ | 5.7 | 1.5 | | 13 | 10 | | | |
| 78½ | 5.6 | .73 | | | 83 | .26 | 2.4 | 78½ | 4.8 | 1.3 | | | | 47 | .29 | 2.0 |
| 84½ | 6.0 | .51 | | | | | | 84½ | 4.8 | .61 | | | | | | |
| 90¼ | 5.6 | .48 | | | 117 | .24 | 2.6 | 90¼ | 4.7 | .81 | | | | 74 | .25 | 2.4 |
| 93¾ | | | 18 | 7.4 | | | | | | | | | | | | |
| 96½ | 5.7 | .35 | | | | | | 96½ | 4.7 | .71 | | 13 | 7.8 | | | |
| 102½ | 4.4 | .23 | | | 142 | .21 | 2.8 | 102½ | 4.2 | .57 | | | | 95 | .23 | 2.3 |
| 114¼ | 4.5 | .04 | | | 179 | .20 | 2.7 | 114¼ | 3.7 | .21 | | | | 130 | .21 | 3.0 |

I = Optical Density 600 nm
II = Glucose % w/v
III = Oxygen Demand ml O$_2$ (STP)/100 ml/hour
IV = Oxygen Transfer Rate ml O$_2$ (STP)/100 ml/hour
V = Consistency Coefficient gm cm$^{-1}$ sec$^{n-2}$
VI = Flow Behaviour Index (n)
VII = Polysaccharide Precipitate % w/v
I = Optical Density 600 nm
II = Glucose % w/v
III = Ammoniacal Nitrogen mg ml$^{-1}$
IV = Oxygen Demand ml O$_2$ (STP)/100 ml/hour
V = Oxygen Transfer Rate ml O$_2$ (STP)/100 ml/hour
VI = Consistency Coefficient gm cm$^{-1}$ sec$^{n-2}$
VII = Flow Behaviour Index (n)
VIII = Polysaccharide Precipitate % w/v

TABLE 3

| LOG HOURS | DRY WEIGHT % w/v | GLUCOSE % w/v | AMMONIACAL NITROGEN mg ml$^{-1}$ | CONSISTENCY COEFFICIENT gm cm$^{-1}$ sec$^{n-2}$ | FLOW BEHAVIOUR INDEX (n) |
|---|---|---|---|---|---|
| 0 | | .08 | .29 | | |
| 4 | | .08 | .26 | .01 | 1 |

TABLE 3-continued

| LOG HOURS | DRY WEIGHT % w/v | GLUCOSE % w/v | AMMONIACAL NITROGEN mg ml$^{-1}$ | CONSISTENCY COEFFICIENT gm cm$^{-1}$ sec$^{n-2}$ | FLOW BEHAVIOUR INDEX (n) |
|---|---|---|---|---|---|
| 8 | | .07 | .26 | .03 | .90 |
| 12 | | .02 | .24 | .08 | .80 |
| 16 | | .03 | .26 | .23 | .70 |
| 20 | | .06 | .19 | .60 | .62 |
| 24 | | .05 | .18 | 1.6 | .56 |
| 27.9 | .21 | .18 | .02 | | |
| 28 | | | GLUCOSE ADDITION | | |
| 28 | | 2.4 | | | |
| 30 | | 1.9 | | | |
| 36 | | 1.5 | | | |
| 40 | | 1.4 | — | | |
| 41¾ | .22 | | | | |
| 44 | | 1.3 | | | |
| 48 | | 1.2 | | 45–50 | 0.25–0.3 |

We claim:

1. A method for the synthesis of polysaccharides comprising culturing polysaccharide-producing microorganisms in a nutrient containing medium, in a first stage involving an increase in the number of microorganisms in said medium by multiplication of said microorganisms, and a second stage in which polysaccharide is synthesized by said microorganisms, said first stage comprising adding carbohydrate capable of supporting polysaccharide biosynthesis to said medium at an exponentially increasing rate, or by using, as sole carbon source, a predetermined quantity of a carbohydrate which does not support polysaccharide biosynthesis, and said second stage being conducted in the absence of at least one nutrient essential for growth of the microorganism.

2. A method as claimed in claim 1 wherein the carbohydrate which does not support polysaccharide biosynthesis is glycerol or xylose.

3. A method as claimed in claim 1 wherein the carbohydrate added at an exponentially increasing rate is glucose.

4. The method as claimed in claim 1 wherein the polysaccharide is xanthan.

5. The method as claimed in claim 4 wherein the microorganism is Xanthomonas.

6. The method as claimed in claim 5 wherein the microorganism is *Xanthomonas campestris*.

7. In a method of synthesis of polysaccharides comprising culturing polysaccharide-producing microorganisms in a medium containing a nutrient essential for growth of said microorganism, whereby growth of said microorganism takes place until said nutrient is exhausted, and said microorganism biosynthesizes said polysaccharide from a carbohydrate source, the improvement in which growth prior to nutrient exhaustion of said microorganism is achieved by adding a predetermined amount of said nutrient essential for growth of said microorganism and a carbohydrate source, said nutrient and carbohydrate source being incapable of supporting biosynthesis of said polysaccharide.

8. In a method for the synthesis of polysaccharides comprising culturing polysaccharide-producing microorganisms in a medium containing a nutrient essential for growth of said microorganism, whereby growth of said microgranism takes place until said nutrient is exhausted, and said microorganism biosynthesizes said polysaccharide from a carbohydrate source, the improvement in which growth prior to nutrient exhaustion of said microorganism is achieved by adding a predetermined amount of a carbohydrate to said medium at a rate that increases exponentially.

* * * * *